US012566138B2

(12) United States Patent
Furrer et al.

(10) Patent No.: US 12,566,138 B2
(45) Date of Patent: Mar. 3, 2026

(54) METHOD FOR RAPID CHARACTERIZATION OF METALLIC POWDERS

(71) Applicant: RTX Corporation, Farmington, CT (US)

(72) Inventors: David U. Furrer, Marlborough, CT (US); Iuliana Cernatescu, Glastonbury, CT (US); Marcel Lucas, Manchester, CT (US); Sergei F. Burlatsky, West Hartford, CT (US)

(73) Assignee: RTX CORPORATION, Farmington, CT (US)

( * ) Notice: Subject to any disclaimer, the term of this patent is extended or adjusted under 35 U.S.C. 154(b) by 108 days.

(21) Appl. No.: 18/415,358

(22) Filed: Jan. 17, 2024

(65) Prior Publication Data

US 2025/0231113 A1    Jul. 17, 2025

(51) Int. Cl.
*G01N 33/202* (2019.01)
*G01N 21/71* (2006.01)

(52) U.S. Cl.
CPC ......... *G01N 21/718* (2013.01); *G01N 33/202* (2019.01); *G01N 2201/06113* (2013.01)

(58) Field of Classification Search
CPC ............... G01N 21/718; G01N 33/202; G01N 2201/06113
See application file for complete search history.

(56) References Cited

U.S. PATENT DOCUMENTS

| | | | |
|---|---|---|---|
| 11,465,240 | B2 | 10/2022 | Liu |
| 2018/0275068 | A1 | 9/2018 | Özcan et al. |
| 2020/0182808 | A1 | 6/2020 | Zhou et al. |

FOREIGN PATENT DOCUMENTS

| | | | | |
|---|---|---|---|---|
| CN | 112661513 A | | 4/2021 | |
| CN | 113684477 A | | 11/2021 | |
| CN | 115144323 A | | 10/2022 | |
| CN | 115773986 A | * | 3/2023 | .............. Y02P 10/25 |
| WO | 2020229838 A1 | | 11/2020 | |

OTHER PUBLICATIONS

Guo et al.; Plasma confinement by hemispherical cavity in laser-induced breakdown spectroscopy; Applied Physics Letters 98, 131501 (2011), 4 pages.

(Continued)

*Primary Examiner* — Jamil Ahmed
(74) *Attorney, Agent, or Firm* — CANTOR COLBURN LLP

(57) ABSTRACT

A method for characterization of metallic powder including presenting a metallic powder sample to a laser and detector system, wherein the metallic powder sample passes through the laser and detector system via a sample introducer; applying a pulsed laser beam to a first location in the metallic powder sample to provide a first micro-plasma at the first location in the metallic powder sample when the pulsed laser beam terminates, the micro-plasma cools to provide spectral emissions at the first location; collecting the spectral emissions at the first location in the metallic powder sample with a detector; analyzing the spectral emissions at the first location to provide a spectral analysis dataset; and identifying inclusions at the first location in the metallic powder sample.

20 Claims, 2 Drawing Sheets

100

101 Present a sample to a laser and detector system via a moving sample introducer.

102 Apply a pulsed laser beam to a first sample location to generate a first micro-plasma.

103 Collect spectral emissions from the first sample location with a detector.

104 Analyze the spectral emissions.

105 Identify inclusions.

106 Characterize the inclusions.

(56)         References Cited

OTHER PUBLICATIONS

Iuga et al.; Electrostatic Separation of Brass from Industrial Wastes; IEEE Transactions on Industry Applications, vol. 35, No. 3, May/Jun. 1999; pp. 537-542.

Iuga et al.; Removal of Metallic Particles From Acrylonitrile Butadiene Styrene Wastes Using Electrostatic Separation Methods; IEEE Transactions on Industry Applications, vol. 47, No. 1, Jan./Feb. 2011; pp. 322-330.

Kiefer et al.; Laser-induced breakdown spectroscopy in gases using ungated detection in combination with polarization filtering and online background correction; Measurement and Science Technology; 21 (2010) 065303 (7pp).

May et al.; Terahertz In-Line Sensor for Direct Coating Thickness Measurement of Individual Tablets During Film Coating in Real-Time; Journal of Pharmaceutical Sciences, vol. 100, No. 4, Apr. 2011; pp. 1535-1544.

Zhang et al.; Stability Enhanced Online Powdery Cement Raw Materials Quality Monitoring Using Laser-Induced Breakdown Spectroscopy; IEEE Photonics Journal; vol. 9, No. 5, Oct. 2017; 11 pages.

Zhou et al.; Laser ablation assisted spark induced breakdown spectroscopy and its application; Frontier of Physics; 15 (5), 52201 (2020); 7 pages.

Cooke et al., "Properties of metal powders for additive manufacturing: a review of the state of the art of metal powder property testing" National Institute of Standards and Technology IR, vol. 7873 (Jul. 2012) pp. 1-28.

Gornushkin et al., "Identification of particulate materials by correlation analysis using a microscopic laser induced breakdown spectrometer" Journal of analytical atomic spectrometry 15.6 (May 2000) pp. 581-586.

Rajavelu et al., "LIBS technique combined with blow gas and vacuum suction to remove particle cloud and enhance emission intensity during characterization of powder samples" Spectrochimica Acta Part B: Atomic Spectroscopy 181 (May 2021): 9 pages.

Sdvizhenskii et al., "Online laser-induced breakdown spectroscopy for metal-particle powder flow analysis during additive manufacturing" Journal of Analytical Atomic Spectrometry 35.2 (Jan. 2020) pp. 246-253.

Search Report issued in European Patent Application No. 25152581. 2; Date of Mailing Jun. 16, 2025 (11 pages).

* cited by examiner

100

101
Present a sample to a laser and detector system via a moving sample introducer.

102
Apply a pulsed laser beam to a first sample location to generate a first micro-plasma.

103
Collect spectral emissions from the first sample location with a detector.

104
Analyze the spectral emissions.

105
Identify inclusions.

106
Characterize the inclusions.

METHOD FOR RAPID CHARACTERIZATION OF METALLIC POWDERS

BACKGROUND

The subject matter disclosed herein generally relates to characterization of metallic powders.

Metal powders are used in many applications, for example, applications in the aerospace industry include nickel-based superalloy turbine engine disks and a range of metallic alloys for additive manufacture. Cleanliness of these powders can impact the performance of the final manufactured components. As the manufacture of metal powders generally involves various handling and processing steps, each step can potentially introduce contamination in the form of non-metallic oxides, complex inorganic compounds, organic compounds, and off-chemistry metallic alloys. In addition to the original manufacture of powders, there is also a need to maintain the cleanliness of powders from additive manufacturing processes that are processed through a recycle path (such as unmelted powders that are reclaimed and re-used in future build campaigns).

Current methods of controlling cleanliness of as-produced metal powder include sieving through screens of known and controlled sizes, or quality monitoring via acid digestion, image analysis, and so forth. Drawbacks of the existing methods include inefficiencies and insufficient analysis. For example, the techniques of acid digestion and image analysis can be used to assess the cleanliness of a metal powder for quality assurance purposes, but these techniques do not provide the capability for separation of unwanted materials from a powder. Sieving can provide control of cleanliness by removal and separation of unwanted particles on the basis of size. In this manner, sieving can provide a means of controlling the maximum size of contaminants that can be introduced into the metallic powder. For sieving techniques, the chemistry of the powder starting material and its contaminants rely on the control of the materials used to produce the powder and the materials in which the powder is permitted to encounter and contact throughout processing. Furthermore, sieving does not generally affect the quantity of foreign material entering the metallic powder, nor does it control the size of final resultant defects formed during manufacture. Therefore, organic particles can decompose into gaseous, reactive, or mobile materials that can react with the metallic powder and contaminate a large volume of the final product.

A need remains for a rapid method to characterize the cleanliness of metallic powders.

SUMMARY

A method for characterization of metallic powder includes presenting a metallic powder sample to a laser and detector system, wherein the metallic powder sample passes through the laser and detector system via a sample introducer; applying a pulsed laser beam to a first location in the metallic powder sample to provide a first micro-plasma at the first location in the metallic powder sample when the pulsed laser beam terminates; the micro-plasma cools to provide spectral emissions at the first location; collecting the spectral emissions at the first location in the metallic powder sample with a detector; analyzing the spectral emissions at the first location to provide a spectral analysis dataset; and identifying inclusions at the first location in the metallic powder sample.

In an embodiment, the sample introducer is a moving conveyor belt, a flowing powder stream, a static surface, a vibratory feeder, a rotating drum, an extruder, a concentrator, or a combination thereof.

In another embodiment, the identifying inclusions at the first location in the metallic powder sample includes comparing spectral emissions of a control sample to the spectral emissions at the first location to determine the presence or absence of inclusions in the metallic powder sample.

In yet another embodiment, the spectral emissions of the control sample are acquired by presenting a control metallic powder sample to the laser and detector system; applying the pulsed laser beam to a location in the control metallic powder sample to provide a control micro-plasma at the location in the control metallic powder sample when the pulsed laser beam terminates; the control micro-plasma cools to provide spectral emissions of the control sample at the location in the control metallic powder sample; and collecting the spectral emissions of the control sample at the location in the control metallic powder sample with the detector.

In yet another embodiment, the method further includes presenting the metallic powder sample to the laser and detector system; applying the pulsed laser beam to a plurality of locations in the metallic powder sample to provide a plurality of micro-plasmas at the plurality of locations in the metallic powder sample, when the pulsed laser beam terminates, the plurality of micro-plasmas cool to provide a plurality of spectral emissions at the plurality of locations in the metallic powder sample; collecting the plurality of spectral emissions at the plurality of locations in the metallic powder sample with a detector; analyzing the plurality of spectral emissions to provide a plurality of spectral analyses datasets; and identifying inclusions at the plurality of locations in the metallic powder sample.

In yet another embodiment, the method further includes presenting the metallic powder sample to a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, or an x-ray computer tomography system; applying energy to the metallic powder sample to provide an energy output of the sample; collecting the energy output of the sample with a second detector; analyzing the energy output to provide an energy output analysis dataset; and combining the information in the spectral analysis dataset and the energy output analysis dataset to identify inclusions in the sample.

In yet another embodiment, the method further includes presenting the metallic powder sample to a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, an x-ray computer tomography system, or a combination thereof; applying a plurality of energy types to a plurality of locations in the metallic powder sample to provide a plurality of energy outputs at the plurality of locations in the sample; collecting the plurality of energy outputs at the plurality of locations in the metallic powder sample with a plurality of detectors; analyzing the plurality of energy outputs to provide a plurality of energy output analyses datasets; and combining the information in the spectral analysis dataset and the plurality of energy output analyses datasets to identify inclusions in the metallic powder sample.

In yet another embodiment, the inclusions are off-chemistry metallic particles, non-metallic particles, or a combination thereof.

In yet another embodiment, the method includes characterization of the inclusions at the location in the metallic powder sample.

In yet another embodiment, the characterization of the inclusions includes chemical characterization of types of non-metallic particles and/or types of off-chemistry metallic particles in the metallic powder sample.

In yet another embodiment, the applying of the pulsed laser beam and the collecting of the spectral emissions are performed in air, under an inert atmosphere, or under reduced pressure.

In yet another embodiment, the inert atmosphere is nitrogen, argon, or a combination thereof, wherein the reduced pressure is partial vacuum of 0.1 kilopascals to 100 kilopascals, or wherein the reduced pressure is a full vacuum of 0.1 pascals to less than 100 kilopascals.

In yet another embodiment, the applying of the plurality of energy types and the collecting of the plurality of energy outputs are performed in air, under an inert atmosphere, under reduced pressure, or a combination thereof.

In yet another embodiment, cleanliness of the metallic powder sample is measured within 30 seconds to 2 days.

A laser and detector system for characterization of metallic powders including a laser source; a sample introducer; a detector; and an analysis system.

In another embodiment, the laser and detector system further includes a plurality of n lasers and a plurality of m detectors.

In yet another embodiment, for the laser and detector system n is 1 to 100 and m is 1 to 100.

In yet another embodiment, the laser and detector system further includes a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, an x-ray computer tomography system, or a combination thereof.

In yet another embodiment, the sample introducer is a conveyor belt, a flowing powder stream, a static surface, a vibratory feeder, a rotating drum, an extruder, a concentrator, or a combination thereof.

In yet another embodiment, the laser and detector system further includes a vacuum pump or a plurality of vacuum pumps capable of providing a reduced pressure of about 100 kilopascals to about 0.1 pascals.

The foregoing features and elements may be executed or utilized in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The subject matter is particularly pointed out and distinctly claimed at the conclusion of the specification. The foregoing and other features, and advantages of the present disclosure are apparent from the following detailed description taken in conjunction with the accompanying drawings in which:

DETAILED DESCRIPTION

Disclosed herein is a method for characterization of metallic powder and a laser and detector system for characterization of metallic powders. The method can be used to identify inclusions (i.e., impurities) in metallic powder samples. The method is particularly suited to rapid on-line or in-line measurement and tracking of cleanliness metrics required for early alerts and warning of quality issues. In this manner corrective actions can be implemented to prevent and reduce impurities in metallic powder samples. The method can be adapted to provide a representative, statistically relevant sampling of locations throughout a sample to accelerate the testing and quality control process. The scope of the characterization of the metallic powder samples can include assessment, detection, identification, and chemical characterization of non-metallic and off-chemistry metallic particles within a sample. A laser and detector system for characterization of metallic powders is also described. The laser and detector system accommodates the characterization of moving throughput of samples or batches of metallic powder. The system can provide representative sample location testing with the capability for traceability of an identified inclusion to a specific location within the tested sample.

"On-line measurement", as used herein, refers to a measurement where 100% of a powder flow in a production line is screened for characterization, where the powder remains within the powder flow in the production line during screening.

"In-line measurement," as used herein, refers to a measurement where a portion of a powder flow is diverted from a production line for characterization. The portion of a powder stream that is diverted can be returned or not returned to the remainder of the powder flow in the production line.

"Off-line measurement", as used herein, refers to a measurement where a portion of a powder flow is diverted from a production line for characterization and the portion of a powder stream that is diverted is not returned to the remainder of the powder flow in the production line.

Figure 1:
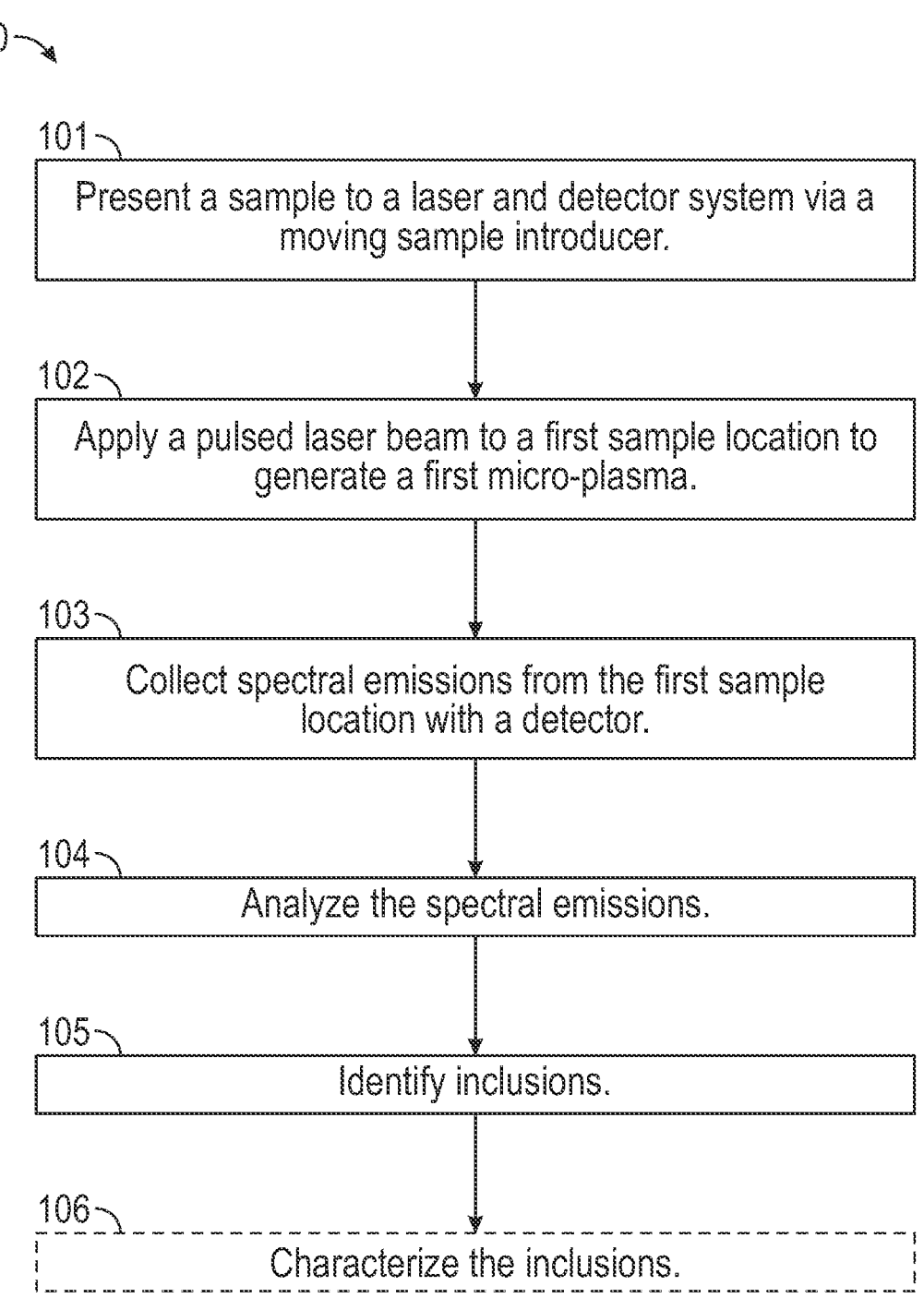
FIG. 1 is a flow diagram illustrating an embodiment of a method for characterization of metallic powder.

An embodiment of the method for characterization of metallic powders (herein after method 100) is illustrated in FIG. 1. The method 100 can be initiated by presenting a sample to a laser and detector system on a sample introducer (step 101). The moving sample can be passed by a pulsed laser beam within the laser and detector system. The pulsed laser beam may be applied to a first location on the moving sample (step 102). During step 102, application of the laser beam to the first location on the moving sample generates a first micro-plasma. When the pulsed laser beam terminates, the first micro-plasma cools to provide spectral emissions at the first location, and the spectral emissions are collected by a detector (step 103) and analyzed (step 104). The analysis of the spectral emission can then be used to identify inclusions at the first sample location (step 105). In some embodiments, the inclusions can be chemically characterized to identify the non-metallic and off-chemistry metallic particles within the moving sample (step 106).

The metallic powder sample types analyzed with the method 100 can include starting materials for aerospace components and metallic alloys for additive manufacturing. Other suitable types of samples include materials acquired post-processing, testing of materials during a processing step, recycled starting materials, and waste materials. The testing of starting materials prior to use or recycled starting materials prior to re-use provides early warning of material quality and sources of contamination. The metallic powder samples can be particles of sizes up to 0.008 inch. For example, the metallic powder samples can be particles of sizes 0.0002 inch to 0.008 inch. The metallic powder can be metal alloys of nickel, aluminum, magnesium, titanium, cobalt, chromium, copper, iron, or combinations thereof. The metallic powder characterized by the method can be used to manufacture a part by additive manufacturing. In some embodiments, the part manufactured by additive manufacturing can have less than 100 parts per million (ppm) of off-chemistry metallic particles and non-metallic particles.

The method can include applying the pulsed laser beam to a plurality of locations in the metallic powder sample to provide a plurality of micro-plasmas at the plurality of locations in the metallic powder sample. The plurality of micro-plasmas can provide a plurality of spectral emissions. The plurality of spectral emissions at the plurality of locations in the metallic powder sample can be collected with a detector. Analysis of the plurality of spectral emissions provides a plurality of spectral analyses datasets, which can be used to identify inclusions at the plurality of locations in the metallic powder sample. Measuring a plurality of locations in the metallic powder sample can increase process throughput and efficiency. Testing of the entire metallic powder sample can be avoided to increase process efficiency. In some embodiments, the method 100 can be used to locate an identified inclusion based on a single, specific location tested within the plurality of locations. The identified and located inclusion can be removed to increase the purity of the metallic powder sample. The quantity of inclusions in the sample can be determined based on their elemental composition.

The method can assess the powder cleanliness at a level that is commensurate with requirements relevant to critical rotating turbine engine parts. In an embodiment, the powder cleanliness can be assessed by detecting the number of inclusions at a selected inclusion particle size by screening a calculated, minimum amount of the metallic powder sample that is statistically representative of the entire sample. For example, the method can detect approximately 10 non-metallic and off-chemistry metallic particles with a diameter of 0.001 inch at a 95% confidence level by screening at least a volume of 1 cubic inch of metallic powder as indicated by a probabilistic model. The statistically representative sample can be the entirety of the metallic powder sample or a portion thereof. The use of a concentrator to systematically increase the concentration of inclusions per powder mass can decrease the statistically representative sample for the method to achieve a similar sensitivity. The method can assess the cleanliness of the statistically representative metallic powder sample within a practical amount of time between 30 seconds and 2 days. In a typical embodiment, the cleanliness assessment can be completed within 1 hour.

The method 100 can include presentation of the metallic powder sample via a sample introducer, wherein the sample introducer is a vibratory feeder, a moving conveyor belt, a flowing powder stream, a static surface, a rotating drum, an extruder, a concentrator, or a combination thereof to facilitate the collection of a plurality of spectral emissions. For example, the sample introducer can include an extruder that churns the powder and pushes it forward in increments also with a static surface in the sample introducer for sample scanning or settling. The sample introducer can include a transparent section within the sample introducer that permits pass through of a laser beam to a sample as it passes through the sample introducer. For example, the rotating drum can include fine mesh sections or transparent windows where a laser beam can pass to reach the sample. The sample can be moved past the laser beam by the sample introducer, or the laser beam can move along the sample within the sample introducer, or the sample can move as the laser also moves. By moving the sample through the laser and detector system the throughput rate of the testing can be increased to provide an efficient testing process. In embodiments wherein the sample introducer is a concentrator, the concentrator can concentrate the contaminants within the sample being tested with a separation process. For example, the concentrator can incorporate an electrostatic separation process inclusions in a bulk sample are concentrated in the sample being tested, in this manner the concentrator can improve the detectability of inclusions within the bulk sample due to their higher concentration in the sample being tested.

In step 105, identifying inclusions at the first location in the metallic powder sample can include comparing control spectral emissions to the spectral emissions of the sample. The comparison of spectral emissions can help identify the presence or absence of inclusions in the metallic powder sample. The control spectral emissions can be acquired by presenting a control metallic powder sample of the desired chemical composition to the laser and detector system. The pulsed laser beam can be applied to a location in the control metallic powder sample to provide a control micro-plasma at the location in the control metallic powder sample. After the pulsed laser beam terminates, the control micro-plasma cools to provide control spectral emissions. The control spectral emissions are collected from the control micro-plasma at the location in the control metallic powder sample by the detector. In some embodiments, the control metallic powder sample can be presented to the laser and detector system and the pulsed laser beam can be applied to a plurality of locations in the control metallic powder sample to provide a plurality of control micro-plasmas at the plurality of locations in the control metallic powder. The plurality of control micro-plasmas can provide a plurality of control spectral emissions. The plurality of control spectral emissions can be collected by a detector. The collection of the plurality of control spectral emissions can provide a more accurate representative average control spectral emission for comparison to the first spectral emission of the metallic powder sample or for comparison to the plurality of spectral emissions of the metallic powder sample.

The method 100 of characterizing metallic powders with a laser and detector system can be conducted with a laser-induced breakdown spectroscopy "LIBS" system. Within a LIBS system, a brief laser pulse is used to ablate a small amount of material on the surface of a sample. The ablated material then interacts with the laser to form a micro-plasma above the sample at the sample/laser incident location. When the laser pulse terminates, the plasma cools in microseconds producing characteristic spectral emissions that are collected by a detector. The collected spectral emissions can be further analyzed for various chemical signatures, such as comparison to a library of elemental emissions stored within the analyzer, comparison to spectral emissions from a control sample, or a combination thereof. Peak intensities within the spectral emissions can be used to quantify the concentrations of elements within the sample. Control spectral emissions of a known inclusion can be used to determine the position and intensities of characteristic peaks for the inclusion. Using the identified characteristic peaks in the control spectral emissions, an acceptance criterion for the intensities of the characteristic peaks can be defined. In this manner, a sample batch can be efficiently screened and passed or failed based on the intensities of the characteristic peaks.

The method 100 can further include presenting the sample to other analysis systems. Suitable analysis systems include a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, or an x-ray computer tomography system. Use of another analysis system can include applying energy to the metallic powder sample to provide an energy output of the sample, collecting the energy output of the sample with a second detector, analyzing the energy output to provide an energy output analysis dataset and combining the information in the spectral analysis dataset and the energy output analysis dataset to more accurately identify and/or characterize the inclusions within the sample. Use of another analysis system may include applying the energy to the same or different location(s) in the sample as tested with the laser and detector system. The method can include the use of a laser and detector system with another analysis system, where the other analysis system applies energy to the metallic powder sample at a plurality of locations in the sample to provide a plurality of energy outputs from the sample. The plurality of energy outputs can be collected with one or more detectors. The plurality of energy outputs are then analyzed to provide a dataset of a plurality of energy output analyses and the dataset of the plurality of energy output analyses can be combined with the dataset of the spectral analysis to identify and/or characterize inclusions in the sample. The combination of techniques can provide a more accurate cleanliness assessment, chemical characterization, mapping of inclusion locations, or a combination thereof.

Figure 2:
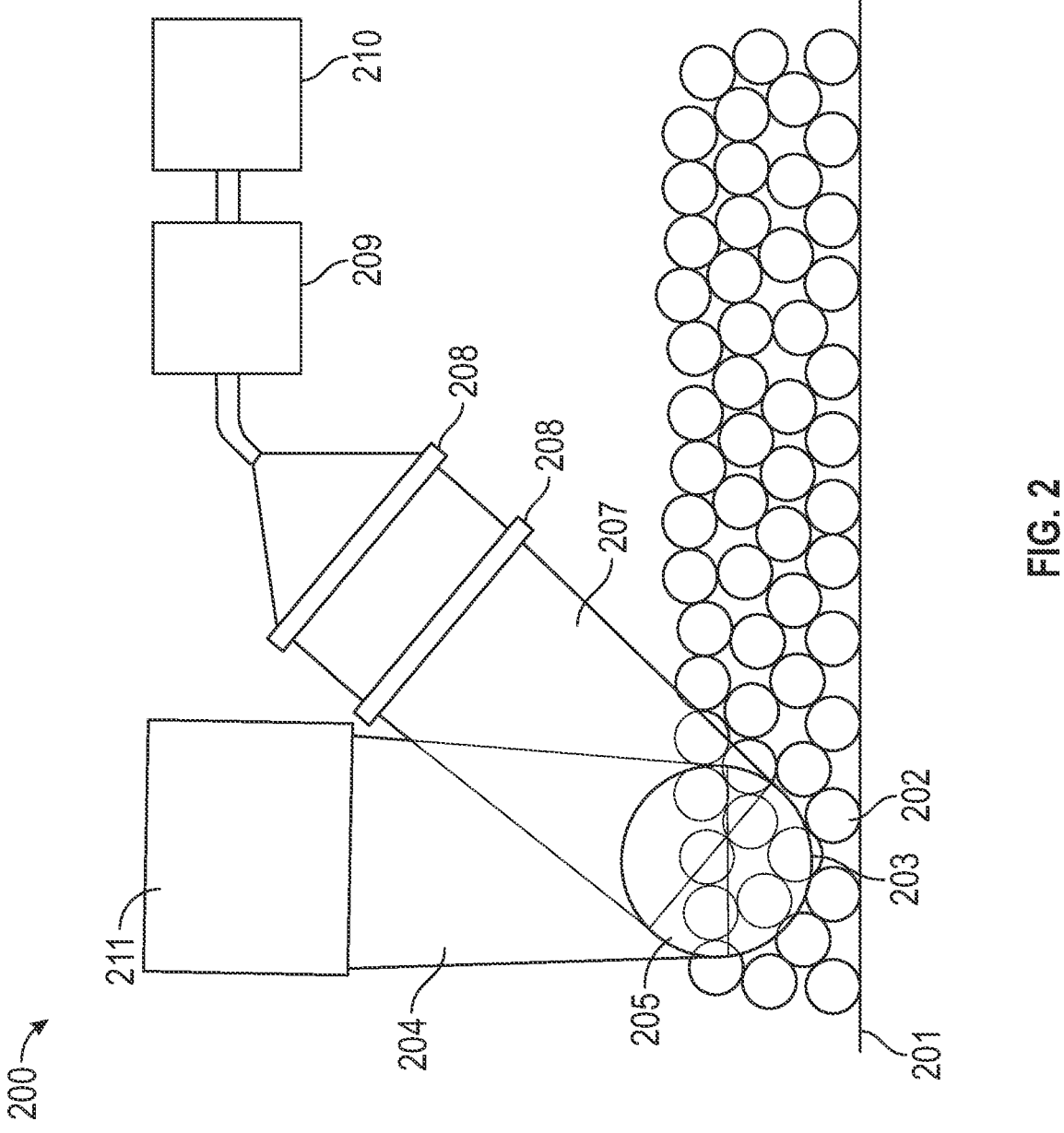
FIG. 2 is a block diagram of an embodiment of a laser and detector system for characterization of metallic powders.

The applying of the pulsed laser beam and the collecting of the spectral emissions can be performed in air, under an inert atmosphere, or under reduced pressure. The inert atmosphere can be nitrogen, a noble gas (e.g., argon), or a combination thereof. The reduced pressure can be a partial vacuum of 0.1 kilopascals to 100 kilopascals and or a full vacuum of 0.1 pascals to less than 0.1 kilopascals. The presenting of the sample can be facilitated by the application of reduced pressure to move the sample, or by the orientation of a sample introducer to flow the sample past the laser beam. The sample can be presented by flowing air with the sample past the laser beam. The laser beam can be focused into a single spot, single area of the sample (as shown in FIG. 2), or the laser beam can be shaped into a line. The laser beam can be split into a plurality of laser beams. The particles can be scanned individually or in a single layer during each laser pulse. In some embodiments, the laser beam can be focused into a larger spot to ablate a larger volume from a grouping of particles. For example, the laser beam can be 2 μm to 5 millimeters (mm) in diameter, or 100 μm to 1 mm in diameter. In another aspect, the laser beam can be in a line of 1 mm by 30 mm as it is focused onto a grouping of particles in the sample. The laser beam can be wide enough to include a collection of particles per laser pulse to increase throughput. The laser pulse shape can be adjusted for non-metallic oxides, complex inorganic compounds, organic compounds, and off-chemistry metallic alloys to optimize the signal-to-noise ratio. For example, the laser pulse can have an energy of 10 microjoules to 1000 millijoules, a pulse duration of 5 nanoseconds (ns) to 20000 ns, and a repetition rate of 1 to 1000 Hz.

The inclusions identified by the method 100 can include off-chemistry metallic particles, non-metallic particles, or a combination thereof. The non-metallic particles can include organic particles and low molecular weight materials. The method 100 can include characterization of the inclusion, such as chemical characterization. The ability to characterize the inclusions can improve process controls, determine impurity sources, facilitate removal of impurities, facilitate neutralization of impurities, and so forth.

An embodiment of a laser and detector system 200 (hereinafter system 200) is provided in FIG. 2. In the system 200, a sample introducer 201 can pass a sample 202 past a laser source (hereafter a laser source or a laser) 211. The laser 211 can provide a pulsed laser beam 204 to ablate a small amount of the sample off a location 203 on the sample surface to provide a micro-plasma 205. When the laser pulse terminates, the micro-plasma cools to produce spectral emissions 207, directed by lenses 208 to a detector 209. The collected spectra emissions can be analyzed by an analyzer 210 to provide a spectral analysis dataset. When the pulsed laser beam ablates a volume from a grouping of particles to generate the micro-plasma 205, the aggregated signal of the ablated volume of the grouping of particles is collected by the detector 209. The signal from the micro-plasma 205 can be collected in reflection mode, where the signal is collected at an angle to the incident laser beam. In some embodiments, the optical system (e.g., lenses) used to focus the laser beam onto the sample surface is also used to collect the spectral emissions, in which case the incident laser and signal collected are colinear.

The system 200 can further include a polarizer to filter out elastic scattering, a spark discharge to enhance plasma emission intensity, plasma confinement to enhance plasma emission intensity, a concave mirror to improve light collection efficiency or a combination thereof. In this manner, the efficiency of the sample throughput can be further increased.

The system 200 can include a plurality of n lasers and a plurality of m detectors. Each of n and m can independently be 1 or as large as practically possible. For example, the system can include up to 100 lasers, including 100 independent laser sources or by splitting a single laser into 100 laser beams. The plurality of n lasers and/or the plurality of m detectors can be moved relative to the sample to accommodate various sampling configurations and sample quantities. The laser(s) and the detector(s) can rotate and translate around the moving sample to collect data and accelerate the data collection process. The analyzer 210 can incorporate software to bin data relative to the tested sample location and the time of data acquisition. In this manner, the system 200 provides the capability for traceability for the data collected back to the specific sample location tested.

The system can include an additional analysis system or a plurality of additional analysis systems. Other analysis systems can include a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, an x-ray computer tomography system, or a combination thereof.

The sample introducer 201 can be a moving or static surface on which the sample is disposed. A static sample can be scanned by a moving laser, or a moving sample can flow past a static laser. The sample introducer 201 can be a conveyor belt, a channel for a flowing sample stream, a static surface, a vibratory feeder, a rotating drum, an extruder, a concentrator, or a combination thereof. For example, the sample can be sprayed on a wide horizontal surface to provide a thin film for sample introduction (a sample introducer) and the laser beam can move along the surface to scan the static sample. In some embodiments, the sample introducer 201 can carry a moving sample through the system 200 as a flowing sample stream. The flow rate of the flowing sample stream can be adjusted by the force of gravity, air flow, pressure gradients (e.g., movement due to an applied vacuum), or a combination thereof. The system 200 can include a vacuum pump or a plurality of vacuum pumps capable of providing reduced pressure of about 100 kilopascals to about 0.1 pascals.

The method and system as disclosed herein can be applied to the analysis of both new metallic powder and reclaimed/recycled metallic powder. Disclosed are means to present a moving sample to a laser and detector, which can be used in-line or on-line to a manufacturing process, a powder reclamation process, an external quality control process, or a combination thereof. For example, the system can be integrated into a powder handling system as a quality control measure during a manufacturing process. Scanning of a sample at selected locations provide for a rapid assessment of the quantity and type of impurities present. While the method can be used to provide a pass/fail check for a metallic sample, the method and system can also be used to determine sources of impurities. Accordingly, the disclosed method and system provide the means to evaluate new processes, equipment, suppliers, and/or for assurance of continued process capability and control.

As used herein, the terms "about" and "substantially" are intended to include the degree of error associated with measurement of the particulate quantity based upon the equipment available at the time of filing the application. For example, the terms may include a range of +8%, or 5%, or 2% of a given value or other percentage change as will be appreciated by those of skill in the art for the particulate measurement and/or dimensions referred to herein.

The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof. It should be appreciated that relative positional terms such as "forward," "aft," "upper," "lower," "above," "below," "radial," "axial," "circumferential," and the like are with reference to normal operational attitude and should not be considered otherwise limiting.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments. Accordingly, the present disclosure is not to be seen as limited by the foregoing description but is only limited by the scope of the appended claims.

What is claimed is:

1. A method for characterization of metallic powder comprising:

presenting a metallic powder sample to a laser and detector system, wherein the metallic powder sample passes through the laser and detector system via a sample introducer, wherein the sample introducer concentrates inclusions within the metallic powder sample;

applying a pulsed laser beam to a first location in the metallic powder sample to provide a first micro-plasma at the first location in the metallic powder sample, when the pulsed laser beam terminates, the micro-plasma cools to provide spectral emissions at the first location;

collecting the spectral emissions at the first location in the metallic powder sample with a detector;

analyzing the spectral emissions at the first location to provide a spectral analysis dataset; and identifying the inclusions at the first location in the metallic powder sample.

2. The method of claim 1, wherein the identifying inclusions at the first location in the metallic powder sample comprises comparing spectral emissions of a control sample to the spectral emissions at the first location to determine the presence or absence of inclusions in the metallic powder sample.

3. The method of claim 2, wherein the spectral emissions of the control sample are acquired by presenting a control metallic powder sample to the laser and detector system;

applying the pulsed laser beam to a location in the control metallic powder sample to provide a control micro-plasma at the location in the control metallic powder sample when the pulsed laser beam terminates, the control micro-plasma cools to provide spectral emissions of the control sample at the location in the control metallic powder sample; and collecting the spectral emissions of the control sample at the location in the control metallic powder sample with the detector.

4. The method of claim 1, further comprising presenting the metallic powder sample to the laser and detector system;

applying the pulsed laser beam to a plurality of locations in the metallic powder sample to provide a plurality of micro-plasmas at the plurality of locations in the metallic powder sample, when the pulsed laser beam terminates, the plurality of micro-plasmas cool to provide a plurality of spectral emissions at the plurality of locations in the metallic powder sample;

collecting the plurality of spectral emissions at the plurality of locations in the metallic powder sample with a detector;

analyzing the plurality of spectral emissions to provide a plurality of spectral analyses datasets; and identifying inclusions at the plurality of locations in the metallic powder sample.

5. The method of claim 1 further comprising presenting the metallic powder sample to a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, or an x-ray computer tomography system;

applying energy to the metallic powder sample to provide an energy output of the sample;

collecting the energy output of the sample with a second detector;

analyzing the energy output to provide an energy output analysis dataset; and combining the information in the spectral analysis dataset and the energy output analysis dataset to identify inclusions in the sample.

6. The method of claim 1 further comprising presenting the metallic powder sample to a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, an x-ray computer tomography system, or a combination thereof;

applying a plurality of energy types to a plurality of locations in the metallic powder sample to provide a plurality of energy outputs at the plurality of locations in the sample;

collecting the plurality of energy outputs at the plurality of locations in the metallic powder sample with a plurality of detectors;

analyzing the plurality of energy outputs to provide a plurality of energy output analyses datasets; and combining the information in the spectral analysis dataset and the plurality of energy output analyses datasets to identify inclusions in the metallic powder sample.

7. The method of claim 1, wherein the inclusions are off-chemistry metallic particles, non-metallic particles, or a combination thereof.

8. The method of claim 1, further comprising characterization of the inclusions at the location in the metallic powder sample.

9. The method of claim 8, wherein the characterization of the inclusions comprises chemical characterization of types of non-metallic particles and/or types of off-chemistry metallic particles in the metallic powder sample.

10. The method of claim 1, wherein the applying of the pulsed laser beam and the collecting of the spectral emissions are performed in air, under an inert atmosphere, or under reduced pressure.

11. The method of claim 10, wherein the inert atmosphere is nitrogen, a noble gas, or a combination thereof, wherein the reduced pressure is partial vacuum of 0.1 kilopascals to 100 kilopascals, or wherein the reduced pressure is a full vacuum of 0.1 pascals to less than 100 kilopascals.

12. The method of claim 6, wherein the applying of the plurality of energy types and the collecting of the plurality of energy outputs are performed in air, under an inert atmosphere, under reduced pressure, or a combination thereof.

13. The method of claim 1, wherein cleanliness of the metallic powder sample is measured within 30 seconds to 2 days.

14. A laser and detector system for characterization of metallic powders comprising:

a sample introducer that concentrates inclusions from the metallic powders;

a laser source for applying a pulsed laser beam to a first location in the metallic powders to provide a first micro-plasma at the first location;

a detector for collecting a spectral emission from the micro-plasma at the first location as the micro-plasma cools; and an analysis system for analyzing the spectral emission at the first location to provide a spectral analysis dataset.

15. The laser and detector system of claim 14, further comprising a plurality of n lasers and a plurality of m detectors.

16. The laser and detector system of claim 15, wherein n is 1 to 100 and m is 1 to 100.

17. The laser and detector system of claim 14, further comprising a spark-induced breakdown spectroscopy system, a laser-induced breakdown spectroscopy system, a near-infrared spectroscopy system, a Raman spectroscopy system, an infrared spectroscopy system, a photoluminescence spectroscopy system, an infrared thermography system, an x-ray fluorescence spectroscopy system, a radiography system, a terahertz spectroscopy system, a fluorescence spectroscopy system, a machine vision system, an ultrasonic testing system, an eddy current testing system, an x-ray computer tomography system, or a combination thereof.

18. The laser and detector system of claim 14, further comprising a vacuum pump or a plurality of vacuum pumps capable of providing a reduced pressure of about 100 kilopascals to about 0.1 pascals.

19. The method of claim 1, further comprising using a concave mirror to improve light efficiency.

20. The method of claim 1, wherein a particle size of the powder is in a range between 0.0002 inches and 0.008 inches.

* * * * *